United States Patent
Genova et al.

(10) Patent No.: US 6,331,511 B1
(45) Date of Patent: Dec. 18, 2001

(54) DETERGENT COMPOSITION WITH A SOFTENING AND PROTECTIVE ACTION OF NATURAL FIBRES

(75) Inventors: Calogero Genova, Vizzolo Predabissi; Giuseppe Giammasi, Melegnano; Francesco Buosi, Milan, all of (IT)

(73) Assignee: Condea Augusta S.p.A., Palermo (IT)

( * ) Notice: Subject to any disclaimer, the term of this patent is extended or adjusted under 35 U.S.C. 154(b) by 0 days.

(21) Appl. No.: 09/349,508

(22) Filed: Jul. 9, 1999

(30) Foreign Application Priority Data

Jul. 10, 1998 (IT) .............................. MI98A1579

(51) Int. Cl.$^7$ ................ C11D 3/20; A61K 7/06
(52) U.S. Cl. .............. 510/119; 510/127; 510/292; 510/327; 510/328; 510/340; 510/394; 510/437; 510/515; 510/522; 510/526; 252/8.63; 252/8.81; 252/8.91; 424/70.1; 514/881
(58) Field of Search .................. 510/119, 127, 510/292, 327, 328, 340, 394, 437, 515, 522, 526; 252/8.81, 8.63, 8.91; 514/881; 424/70.1

(56) References Cited

U.S. PATENT DOCUMENTS

| | | | |
|---|---|---|---|
| 3,953,353 | * 4/1976 | Barrett, Jr. et al. | 510/283 |
| 4,981,845 | * 1/1991 | Pereira | 514/557 |
| 5,409,630 | * 4/1995 | Lysy et al. | 510/401 |
| 5,728,732 | * 3/1998 | Corey et al. | 514/544 |
| 5,741,497 | * 4/1998 | Guerrero et al. | 424/401 |
| 5,880,076 | * 3/1999 | Vermeer | 510/123 |
| 5,882,661 | * 3/1999 | Dorogi et al. | 424/401 |
| 5,912,002 | * 6/1999 | Grieveson et al. | 424/401 |
| 5,961,992 | * 10/1999 | Ilardi et al. | 424/401 |
| 5,962,391 | * 10/1999 | Oldenhove | 510/369 |
| 6,048,520 | * 4/2000 | Hoshowski | 424/70.17 |

FOREIGN PATENT DOCUMENTS

| | | | |
|---|---|---|---|
| 0692244 | * | 1/1996 | (EP) . |
| 51145412-A | * | 12/1977 | (JP) . |
| 90/06105 | * | 6/1990 | (WO) . |
| WO-94/10274-A1 | * | 5/1994 | (WO) . |
| 95/05160 | * | 2/1995 | (WO) . |
| 98/56333 | * | 12/1998 | (WO) . |
| 98/56337 | * | 12/1998 | (WO) . |

OTHER PUBLICATIONS

Matssura, N. et al. "Study of Headspace Analysis of Different Shampoo Base Formulations", Sci. Conf. Asian Soc. Cosmet. Sci., 3rd ED., 1997, pp. 205–208 (Abstract Only).*

* cited by examiner

*Primary Examiner*—Lorna M. Douyon
(74) *Attorney, Agent, or Firm*—Oblon, Spivak, McClelland, Maier & Neustadt, P.C.

(57) ABSTRACT

A detergent composition with a softening and protective action of natural fibers, wherein the composition has no cationic surface-active agents, and contains:

(a) surface-active agents selected from the group including anionic, nonionic and amphoteric surface-active agents and relative mixtures;

(b) esters having the formula (I):

$$R^1\text{—CO—O—(—CH}_2\text{—CH}_2\text{—O—})_a\text{—R}^2 \qquad (I)$$

wherein:
a is between zero and 20;
$R^2$ is a mono-functional hydrocarbon radical, having from 6 to 20 carbon atoms;
$R^1$ is a mono-functional hydrocarbon radical defined in the claims.

14 Claims, No Drawings

DETERGENT COMPOSITION WITH A SOFTENING AND PROTECTIVE ACTION OF NATURAL FIBRES

The present invention relates to a detergent composition with a softening and protective action of natural fibers.

Softening compositions are widely used for domestic detergents for improving the softness of delicate fabrics (wool and silk). These compositions mainly consist of aqueous emulsions which cannot be used in the actual washing phase, but only in the final rinsing phase. This is mainly due to the incompatibility of the softening agents widely used, consisting of quaternary ammonium salts, particularly dimethyl ditallowyl ammonium chloride (DDTAC) and distearyl ammonium chloride. The above quaternary salts, in the presence of anionic surface-active agents, would produce compounds insoluble in water with a consequent loss in effectiveness of the softening action.

The high effectiveness of these ammonium derivatives has the disadvantage of the toxicological aspect of these products and particularly their high aquatic toxicity which has recently considerably restricted their use in the formulation of domestic detergents. This has led to the search for new softening substances with an environmental impact which is more acceptable to the community. The importance given to this problem has led to the development of products alternative to quaternary ammonium salts having either equivalent performances or a lesser ecotoxicological impact.

In this respect, various patent documents which have appeared recently, can be mentioned.

For example U.S. Pat. No. 5,290,459 describes the use of partial esters of pentaerythritol or partial esters of ethoxylated oligomers of pentaerythritol to be used as such or combined with bentonites for the preparation of aqueous emulsions to be used as softening agents to be added in the rinsing phase of the washing cycle.

U.S. Pat. No. 3,928,212 on the other hand discloses the use of esters of fatty acids of polyhydric alcohols as softening agents to be used as an emulsion in the rinsing phase.

U.S. Pat. No. 4,126,562 describes the use of esters of higher fatty acids mixed with quaternary ammonium salts as softening agents with a low content of quaternary ammonium salts.

U.S. Pat. No. 4,142,978 discloses the use of esters of sorbitol as alternative softening agents to quaternary ammonium salts.

U.S. Pat. No. 4,162,984 describes the use of mixtures consisting of ammonium salts of alkyl imidazoline and esters of fatty acids (mono or dicarboxyl, alkyl or aromatic) of polyhydric alcohols.

DE-A-3,612,479 discloses the use of softening agents for the textile industry consisting of mixtures of quaternary ammonium salts and esters of polyhydric alcohols.

The state of the art described above, although on the one hand reducing the quantity of nitrogenated derivatives as softening agents for natural fibers, does not allow, on the other hand, similar performances to those of nitrogenated derivatives as such to be obtained.

In any case the compositions described in the above patents have worse performances with respect to quaternary ammonium salts.

A detergent composition with a softening and protective action of natural fibers has now been found which overcomes the disadvantages described above and at the same time has softening properties equivalent to or higher than the quaternary ammonium salts normally used for this purpose.

In accordance with this, the present invention relates to a detergent composition with a softening and protective action of natural fibers, preferably keratinous, characterized in that it has no cationic surface-active agents, and comprises:

a) surface-active agents selected from anionic, non-ionic and amphoteric surface-active agents and relative mixtures, preferably anionic;

(b) esters having general formula (I):

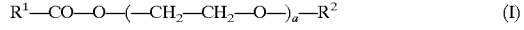

$$R^1\text{—CO—O—}(\text{—CH}_2\text{—CH}_2\text{—O—})_a\text{—}R^2 \qquad (I)$$

wherein:

a is between zero and 20, preferably zero;

$R^2$ is a mono-functional hydrocarbon radical, preferably alkyl, having from 6 to 20, preferably from 8 to 18, carbon atoms;

$R^1$ is a mono-functional hydrocarbon radical containing at least one hydroxyl and a number of carbon atoms equal to or higher than two, preferably selected from:

c1) —$C_6H_n(OH)_m$, wherein n is between 3 and 4, m is between 1 and 2, the sum of m+n being equal to 5, preferably —$C_6H_4(OH)$;

c2) —CH(OH)—CH($R^3$)—COO—(—$CH_2$—$CH_2$—O—)$_{a'}$, —$R^4$, wherein $R^3$=H or OH; a' is between 0 and 20, and is preferably zero, and $R^4$ is a mono-functional hydrocarbon radical, preferably alkyl, having from 6 to 20, preferably from 8 to 18, carbon atoms;

c3) —CH(OH)—$CH_3$;

the weight ratio between the surface-active agents (a) and the esters having general formula (I) ranging from 1/1 to 600/1, preferably from 1.5/1 to 400/1.

The various groups of surface-active agents (a) are well known to experts in the field.

Typical but non-limiting examples of anionic surface-active agents are alkyl sulfates, alkyl hetero sulfates, alkyl- (also called alkan-) sulfonates, alkylaryl sulfonates, alkyl carboxylates, alkylhetero carboxylates, sulfonated alpha-olefins, sulfonated internal olefins.

Typical but non-limiting examples of non-ionic surface-active agents are alkylpolyglucosides, alkylpolyethoxylates, alkylaryl polyethoxylates.

Typical but non-limiting examples of amphoteric surface-active agents are alkyl-amido propyl betaine and alkyl betaine.

With respect to $R^2$ and $R^4$, typical examples of alcohols having the general form $R^2OH$ and $R^4OH$ are capronic alcohol, capryl alcohol, 2-ethylhexyl alcohol, caprinic alcohol, lauryl alcohol, isotridecyl alcohol, myristic alcohol, cetyl alcohol, palmitic alcohol, stearic alcohol, isostearic alcohol, oleic alcohol, linoleic alcohol, linear or branched alcohols obtained synthetically according to the oxo or modified oxo or Ziegler or Guerbet process, and the relative mixtures. Technical aliphatic alcohols have from 8 to 32 carbon atoms of a synthetic or natural derivation, are preferably used.

As far as the esters have general formula (I) are concerned, typical examples of these esters are:

tridecyl salicylate (compound having general formula (I) wherein a=0, $R^2=C_{13}$ alkyl, $R^1$=—$C_6H_4OH$);

di-($C_{12}$–$C_{13}$) alkyl malate (compound having general formula (I) wherein a=0, $R^2$=mixture of $C_{12}$–$C_{13}$ alkyls, $R^1$ =—CH(OH)—$CH_2$—$COOR^2$);

di-($C_{12}$–$C_{13}$)alkyl tartrate (compound having general formula (I) wherein a=0, $R^2$=mixture of $C_{12}$–$C_{13}$ alkyls; $R^1$=—CH(OH)—CH(OH)—$COOR^2$);

($C_{12}$–$C_{13}$) alkyl lactate (compound having general formula (I) wherein a=0, $R^2$=$C_{12}$–$C_{13}$; $R^1$=—CH(OH)—

CH$_3$); The esters having general formula (I) can be prepared according to techniques well known to experts in the field. In particular they can be prepared by the esterification of fatty alcohols or fatty alcohols ethoxylated with the corresponding hydroxyacids.

The composition of the present invention can be used in various formulations with different applications.

A first application is in domestic detergents. In this case the detergent formulation with a softening effect (formulation A) comprises surface-active agents (a) and esters having general formula (I), the ratio between the two being from 200/1 to 5/1, preferably from 100/1 to 10/1. The surface-active agents which can be used in the above composition can be selected from sulfate alcohols, ethoxysulfate alcohols, sulfonated alkylbenzene, ethoxylated alcohols, ethoxylated alkylaryl, amphoteric surface-active agents (betaine) and/or alkylpolyglucosides (APG), sulfonated internal olefins, sulfonated alpha-olefins. In the above formulation A, the concentration of surface-active agents can vary from 10 to 40% by weight, the complement to 100, regardless of the esters of the present invention, consisting of water and minor components such as antifoaming agents, perfumes and preservatives, usually used in commercial formulations.

A second application is as a softening agent in the rinsing phase. In this case the formulation (formulation B) has a ratio between surface-active agents (a) and esters having general formula (I) ranging from 50/1 to 0.75/1, preferably from 20/1 to 1.5/1. In this case the surface-active agents can be selected from sulfonated alkylbenzenes, ethoxylated alcohols and ethoxylated alkyl aryl having HLB ranging from 8 to 15, sulfonated internal olefins, sulfonated alpha-olefins, and relative mixtures. In the case of this formulation B, the weight concentration of the surface-active agents ranges from 2 to 8% by weight, the complement to 100 being of water and minor components.

A third application is in textile finishing for improving the surface properties of natural and synthetic fibers (friction coefficient, feel). In this case the formulation (formulation C) has a ratio between surface-active agents (a) and esters having general formula (I) ranging from 10/1 to 1.5/1, preferably from 5/1 to 2/1. The surface-active agents are selected from alkylbenzenesulfonates, ethoxylated alcohols and alkylaryl ethoxylates having an HLB ranging from 8 to 15, sulfonated internal olefins and relative mixtures. Fatty alcohols ($C_{11}$–$C_{22}$) and relative mixtures can be used as emulsion stabilizers. In the case of this formulation C, the concentration of surface-active agents can vary from 3 to 10%, the complement to 100 consisting of water and minor components.

A fourth application is in the field of hair shampoos. In this case the formulation (formulation D) has a ratio between surface-active agents (a) and esters having general formula (I) ranging from 100/1 to 10/1, preferably from 40/1 to 5/1. In this case the surface-active agents are selected from sulfate alcohols, ethoxysulfate alcohols, amphoteric surface-active agents (betaine), alkylpolyglucosides (APG), sulfonated internal olefins, sulfonated alpha-olefins and relative mixtures. In this formulation D, the concentration of surface-active agents ranges from 7 to 20% by weight, the complement to 100 consisting of water and minor components.

The following examples provide a better illustration of the present invention.

EXAMPLES

Table 1 provides some formulation examples containing fatty esters deriving from alpha-hydroxyacids (malic acid), or from beta-hydroxyacids (salicyl acid), relating to typical formulates of detergents for both hand and machine washing based on the most common and widely used anionic surface-active agents used in the field.

These formulations were used for the machine washing of natural fibers (Merino wool and Silk crepe) to evaluate their softness, the degradation degree after repeated washing as well as the resistance of the fibers after various washing cycles and prolonged exposure to light radiation. Each washing was carried out on a load of 2.5 Kg. Using 50–80 grams of liquid detergent. The load consisted of 2 samples of woollen fabric (70cm×70cm), 2 samples of silk fabric (70cm×70cm) and cotton fabric up to a total load of 2.5 kg.

TABLE 1

| Component | A19 | A23 | A24 |
|---|---|---|---|
| | Concentration w/w % | | |
| Sodium lauryl ether sulfate | 12.0 | 12.0 | 6.0 |
| Sodium alkylbenzenesulfonate | — | — | 5.8 |
| Lialet 5E0 | 3.0 | 3.0 | 3.0 |
| Sodium lauryl sulfate | 5.0 | 5.0 | 5.0 |
| Sodium Citrate | 0.1 | 0.1 | 0.1 |
| Perfume | 0.25 | 0.25 | 0.25 |
| ($C_{12}$–$C_{13}$) alkyl malate | 0.5 | — | — |
| Tridecyl salicylate | — | 0.5 | 0.5 |
| Preservative | 0.1 | 0.1 | 0.1 |
| Opacifier | 0.8 | 0.8 | 0.8 |
| Antifoaming agent | 1.0 | 1.0 | 1.0 |
| Water | to 100 | to 100 | to 100 |
| pH | 7.5 | 7.5 | 7.5 |

The formulations indicated in Table 1 were compared with three commercial products of leading companies in the field, based on substantially different formulation principles.

In fact the formulations P1 and P2 base their softening action on amphoteric surface-active agents combined with small quantities (<1%) of a proteic agent (lanolin, P1) and quaternary ammonium salts (P2). The formulation P3, as it mainly consists in its surface-active base of polyethoxylated non-ionic surface-active agents, carries out its softening action with a considerable quantity of quaternary ammonium salts.

Table 2 indicates the basic components of the formulations of the commercial products specified in the corresponding labels.

TABLE 2

| | P1 | P2 | P3 |
|---|---|---|---|
| SURFACE-ACTIVE AGENTS | | | |
| Anionic | <5.0 | <5.0 | <5.0 |
| Amphoteric | <5.0 | 5–15 | — |
| Ethoxylates | <5.0 | <5.0 | 15–30 |
| SOFTENING AGENT | | | |
| Lanolin | YES | — | — |
| Cation. surf.-act. agents | — | — | >5 |
| Not specified | — | YES | — |

As can be seen from Table 2, the presence of proteic agents (lanolin) or of small doses of non-specified softeners as they are less than 1% by weight, is associated with the use of amphoteric surface-active agents.

For the formulation containing non-ionic surface-active agents (P3), the concentration of ammonium derivatives as softening agent is quite significant.

After 10 and 15 washing cycles, the following physical parameters, listed hereunder, of the fabric, were evaluated, according to standard procedures with reference to official organisms:

| | | |
|---|---|---|
| 1. | Breaking load | (Method UNI 1932); |
| 2. | Impact strength | (Method UNI 1932); |
| 3. | Deformation | (Method UNI 1932); |
| 4. | Young's modulus | (Method UNI 1932); |
| 5. | Warp and filling recovery angle | (EN-ISO 22313); |
| 6. | Light radiation stability after 50 hours | (EN-ISO 22313). |

In addition, Softness Tests were carried out according to a procedure which is described hereunder.

RESULTS

10 Machine Washings

Although the surface-active base of the formulations containing fatty esters of alpha or beta hydroxyacids, of the present invention, consists of anionic surface-active agents (known as being amongst the most aggressive towards natural fibers), the natural fibre properties observed after 10 consecutive washings did not undergo any significant variation. In fact, on evaluating the variations in the breaking load of the fibre and its elastic deformation both for Merino wool (Tab. 3) and Silk crepe (Tab. 4), with respect to the non-washed fabric, there are no substantial variations in the physical properties of the natural fibers. The fibers, in fact, remain intact and resistant to stretching, as can be observed from the recovery angle value indicated.

The results obtained are in line with those observed for the same fabrics washed with the commercial product P1 based on amphoteric surface-active agents and lanolin.

TABLE 3

MERINO WOOL after 10 consecutive washings

| | As such | A19 | A23 | A24 | P1 |
|---|---|---|---|---|---|
| Load (kgf) | 0.093 | 0.081 | 0.088 | 0.081 | 0.094 |
| Deformation (%) | 13.602 | 14.063 | 15.111 | 16.130 | 15.598 |
| Recovery Angle | | | | | |
| Warp | 159.6 | 161.3 | 154.6 | 162.0 | 159.6 |
| Filling | 163.0 | 159.3 | 151.3 | 158.6 | 159.0 |

TABLE 4

White silk crepe after 10 consecutive washings

| | As such | A19 | A23 | A24 | P1 |
|---|---|---|---|---|---|
| Load (kgf) | 0.151 | 0.144 | 0.149 | 0.147 | 0.142 |
| Deformation (%) | 17.572 | 20.138 | 19.363 | 17.256 | 17.402 |
| Recovery Angle | | | | | |
| Warp | 142.3 | 152.3 | 159.0 | 164.3 | 153.0 |
| Filling | 140.3 | 156.3 | 157.3 | 169.3 | 151.3 |

However, after 10 washings in a washing-machine, subjecting the fabrics to prolonged exposure to light radiation of 50 hours, there were significant variations in behaviour between the formulations tested (see Table 5).

TABLE 5

MERINO WOOL after 10 washings. Light radiation effect (50 hours).

| | A 24 | | | A 23 | | | P1 | | |
|---|---|---|---|---|---|---|---|---|---|
| Radiation | 0 | 50 | Δ % | 0 | 50 | Δ % | 0 | 50 | Δ % |
| Load | .081 | .094 | 8.9 | .088 | .091 | 3.4 | .094 | .088 | −6.4 |
| Deform. | 16.13 | 16.15 | .01 | 15.11 | 15.25 | .9 | 15.60 | 18.01 | 15.34 |

With respect to Merino Wool fabric (Table 5), the formulations containing the fatty ester of salicyl acid registered a tendential increase in the breaking load of the fibre (greater tensile strength) combined with an intact elastic deformation (greater deformation resistance) with respect to what was observed for the same fabric washed with the comparative formulation P1. For this latter formulation, there was both a tendential decrease in the breaking load (lower tensile strength) and a significant variation in the elastic deformation, indicating a greater deformation facility. It should be pointed out that the optimum elastic deformation range of woollen fibers varies from 10 to 18. At levels lower than 10 the fibre tends to be too rigid, at values higher than 18, the fibre tends to yield and consequently lose its natural structure.

Also in the case of the Silk Crepe fabric (Table 6) there were tendential differences in behaviour. Whereas the fabric washed with the commercial product P1 shows a distinct reduction in the elastic deformation, the fabric washed with the formulations containing the fatty ester of salicyl acid according to the present invention, has a lesser alteration in its elastic deformation. The fabric with the least elastic deformation of all is that washed with the formulation A23.

TABLE 6

White Silk crepe after 10 washings and light radiation (50 hours).

|  | A 23 | | | A 24 | | | P1 | | |
|---|---|---|---|---|---|---|---|---|---|
| Radiation | 0 | 50 | Δ % | 0 | 50 | Δ % | 0 | 50 | Δ % |
| Load | 0.149 | 0.135 | −9.4 | 0.147 | 0.139 | −5.4 | 0.142 | 0.132 | −7.0 |
| Deform. | 19.363 | 16.697 | −13.7 | 17.26 | 14.04 | 18.7 | 17.402 | 12.418 | −28.6 |

The softness evaluation of the fabrics was effected by 10 experts of whom each one gave a value of 1 to 5:

1=rough, void, papery, unpleasant feel, different from the fabric as such;

5=smooth, soft, full, pleasant feel, the same as the fabric as such.

The results of the Softness Panel (Table 7) gave very positive results for the softness and feel of the formulations containing fatty esters of alpha or beta hydroxyacids.

In particular the formulation A24 gave the fabrics an excellent softness and feel level which was higher than the other formulations tested, comprising the commercial product P1 which obtained quite a high result.

TABLE 7

Softness Panel

|  | A19 | A23 | A24 | P1 |
|---|---|---|---|---|
| MERINO WOOL | 3 | 4 | 5 | 5 |
| SILK CREPE | 3 | 4 | 5 | 4 |

The protective action on natural fibers of salicyl ester appears even more evident from the Panel values provided in Table 7a which compares woollen and silk fabrics washed with the formulation A24 and a formulation consisting of the same composition, without salicyl ester.

TABLE 7a

|  | A24 without salicyl ester | A24 |
|---|---|---|
| WOOL | 2 | 5 |
| SILK | 1 | 5 |

As can be seen from Table 7a, salicyl ester is capable of distributing itself between the detergent phase and the natural fibre substrate to such a degree as to prevent the abrasive action of the surface-active mixture.

15 Machine Washings

With an extension to 15 machine washings, no particular deterioration phenomena of the natural fibers were observed.

Although the formulations of the present invention are based on anionic surface-active agents which are aggressive for natural fibers, and in spite of the low content of fatty esters of alpha or beta hydroxyacids (as softening-protective agent), the mechanical resistance and elasticity properties, except for a few exceptions, show a satisfactory degree of integrity after 15 washings.

With respect to Merino Wool (see Table 8), whereas the ultimate elongation remains more or less unaltered also for fabrics washed with water alone, the elastic deformation varies significantly with a variation in the detergent formulation used. In fact, whereas washing with water alone or with the commercial product P3 reveals a significant destructuring action of the natural fibers (value >18; upper limit of the optimum elastic deformation range), the use of the formulations containing fatty esters of alpha or beta hydroxyacids, as also the commercial product P2, does not substantially modify the elastic properties of the fibers as the values obtained fall within the optimum elastic deformation range.

Also in this case, the woollen fabrics conserve, and in some cases improve, their already good workability properties for the ironing of the original fabric.

TABLE 8

MERINO WOOL after 15 washings

|  | As such | A19 | A23 | A24 | P2 | P3 | Water |
|---|---|---|---|---|---|---|---|
| Load | 0.093 | 0.095 | 0.089 | 0.091 | 0.100 | 0.099 | 0.103 |
| Deform. | 13.602 | 13.78 | 18.0 | 15.416 | 15.108 | 19.357 | 19.346 |
| Recovery Angle | | | | | | | |
| Warp | 159.6 | 158.0 | 165.6 | 159 | 155.3 | 168.3 | 155.3 |
| Filling | 163 | 161.3 | 154.3 | 158.6 | 155.0 | 157.3 | 155.3 |

With respect to the silk fabric (Table 9), analogous conclusions can be made to those for the Merino Wool. The breaking load (mechanical resistance) of the fibre is slightly reduced, but to the same degree for all the detergent formulations used, comprising water. This indicates that the mechanical friction of the fabrics during washing causes a destructuring effect of the keratinous fibers with a consequent reduction in their mechanical resistance.

As far as the elastic deformation of Silk crepe is concerned, it should be noted that, analogously to Merino Wool, whereas washings with water alone cause a significant alteration in the elasticity of silk, washing with the formulations containing the softening agent showed a reasonable protective effect. In particular, the formulations containing esters of alpha or beta hydroxyacids even if at very low concentrations, prove to be more effective than the comparative commercial products, as the Silk Crepe fabric is decisively more elastic.

From the Recovery Angle values, it can be seen that the fabric even after 15 washings maintains an excellent crease-resistance, as these values are very close to the value of 180 which represents the optimum value.

TABLE 9

White Silk Crepe after 15 washings

|         | As such | Water | A19   | A23   | A24   | P2    | P3    |
|---------|---------|-------|-------|-------|-------|-------|-------|
| Load    | 0.151   | 0.131 | 0.129 | 0.130 | 0.128 | 0.127 | 0.129 |
| Deform. | 17.57   | 11.41 | 13.61 | 16.36 | 13.82 | 12.29 | 12.88 |

Recovery Angle

|         | As such | Water | A19   | A23   | A24   | P2    | P3    |
|---------|---------|-------|-------|-------|-------|-------|-------|
| Warp    | 142.3   | 146.0 | 158.0 | 158.3 | 150.6 | 160.3 | 152.3 |
| Filling | 140.3   | 148.3 | 138.6 | 160.0 | 153.3 | 154.0 | 144.0 |

The stability of the fabrics to light radiation, even after 15 washings, proved to be particularly satisfactory. From the data of Table 10 it can be clearly seen how the breaking load of the wool does not undergo any particular variations for all the formulations tested (comprising washing with water alone), whereas the elastic deformation of the wool, after prolonged exposure to light, remains practically unaltered for the fabrics washed with the formulations A23, A24 (containing fatty ester of salicyl acid) and P2. For the washings with water alone, the value obtained shows a greater yield of the same fibre, whereas for the fabrics washed with the formulation P3 a drastic variation is observed with respect to the non-exposed fabric, indicating a particular lack of protection of the proteic structure from photonic radiation action.

TABLE 10

MERINO WOOL after 15 washings and light radiation (50 hours)

|       | A23   |       | A24   |       | P2    |       | P3    |       | Water |       |
|-------|-------|-------|-------|-------|-------|-------|-------|-------|-------|-------|
| Rad.  | 0     | 50    | 0     | 50    | 0     | 50    | 0     | 50    | 0     | 50    |
| Load  | 0.089 | 0.087 | 0.091 | 0.087 | 0.10  | 0.097 | 0.099 | 0.089 | 0.103 | 0.096 |
| Def.  | 18.0  | 17.4  | 15.4  | 14.4  | 15.1  | 14.0  | 19.4  | 14.0  | 19.4  | 0.7   |

Also prolonged radiation of the Silk Crepe fabrics registered (see Table 11) decisively positive elastic deformation values for the fabrics washed with the formulations containing fatty ester of salicyl acid. In fact, after 50 hours of light exposure, as indicated in Table 11, the values obtained for these fabrics are much higher than those recorded for the formulations of the commercial products P2 and P3.

TABLE 11

SILK CREPE after 15 washings and light radiation (50 hours).

|         | A23   |       | A24   |       | A19   |       |
|---------|-------|-------|-------|-------|-------|-------|
| Radiat. | 0     | 50    | 0     | 50    | 0     | 50    |
| Load    | 0.130 | 0.119 | 0.128 | 0.125 | 0.129 | 0.125 |
| Deform. | 16.4  | 13.5  | 13.8  | 12.8  | 13.3  | 12.8  |

|         | P2    |       | P3    |       | Water |       |
|---------|-------|-------|-------|-------|-------|-------|
| Radiat. | 0     | 50    | 0     | 50    | 0     | 50    |
| Load    | 0.127 | 0.116 | 0.129 | 0.118 | 0.131 | 0.117 |
| Deform. | 12.3  | 11.3  | 12.9  | 10.8  | 11.4  | 11.1  |

Finally, evaluation of the conservation state of the fabrics after 15 consecutive washings by the Softness Panel test (Table 12) demonstrated that, apart from the satisfactory protective properties of the keratinous fibres, the formulations containing salicyl ester of the present invention give natural fabrics (comprising cotton) a particularly satisfactory softness degree which is even higher than the formulations of the commercial products. This is possible even in the presence of anionic surface-active agents (known for their aggressiveness towards natural fabrics) and with a low concentration of compounds having general formula (I).

TABLE 12

Softness Panel test after 15 washings

|  | A19 | A23 | A24 | P2 | P3 | Water |
|---|---|---|---|---|---|---|
| Merino Wool | 3 | 5 | 5 | 3.5 | 5 | 3 |
| Silk Crepe | 3.5 | 3.5 | 4.5 | 4 | 4 | 3 |
| Cotton | 3.5 | 4 | 4 | 3.5 | 4 | 2.5 |

TESTS EFFECTED ON HAIR

The evaluation of a control formulation (corresponding to a commercial product called Gafquat$^R$ 755 N, active part Poliquaternium$^R$ 11) and three formulations of the present invention called ETI (dialkyl tartrate), EMI (dialkyl malate), ESI (tridecyl salicylate), was carried out on 20 volunteers. The composition of the above formulations is indicated in Table 13.

TABLE 13

Test effected on hair

|  | Name | Cont. | ETI | EMI | ESI |
|---|---|---|---|---|---|
| TEXPON ® NSO | Laurylether sulfate | 8.1 | 8.1 | 8.1 | 8.1 |
| Tego ® Betain L7 | Alkylamide propyl betain | 1.5 | 1.5 | 1.5 | 1.5 |
| GAFQUAT ® 755 N | Poliquaternium 11 | 0.3 |  |  |  |
| ETI | di-($C_{12}$–$C_{13}$) alkyl tartrate |  | 0.3 |  |  |
| EMI | di-($C_{12}$–$C_{13}$) alkyl malate |  |  | 0.3 |  |
| ESI | Tridecyl Salicylate |  |  |  | 0.3 |
| Eukyl ® K400 | Preservative | 0.2 | 0.2 | 0.2 | 0.2 |
| Perfume |  | 0.2 | 0.2 | 0.2 | 0.2 |
| Water |  | 87.2 | 87.2 | 87.2 | 87.2 |
| Sodium chloride |  | 2.5 | 2.5 | 2.5 | 2.5 |

The tricological parameters of the study (see table 14) refer to the state of both wet hair and dry hair. Particular attention is paid to:

a. Combability of wet hair (to show the incidence of the formation of knots during the washing phase, index of low hair greasiness);
b. Feel of wet hair (index of conditioning effect);
c. Combability of dry hair (index of sufficient hair greasiness which can be associated with a lower formation of electrostatic charges);
d. Anti-electrostatic effect (index of greater facility in desired combing);
e. Feel of dry hair (index of the silkiness and consequently pleasant feel of the hair, very important for acceptance on the part of the consumer);
f. Easy handling (index of the facility for hair setting and combing);
g. Duration of wave-sets (index of the capacity of the hair to maintain sets effected by hair-dressers).

The scale of values used by experts are as follows:
1 Excellent;
5 Poor;
except for the antistatic effect for which:
  1 represents no electrostatic effect;
  5 strong electrostatic effect.

TABLE 14

Summary of Half Head Test results

|  | Cont | EMI | Cont | ETI | Cont | ESI |
|---|---|---|---|---|---|---|
| Gloss | 2.4 | 2.3 | 2.3 | 2.2 | 2.5 | 2.5 |
| Wet hair combability | 2.3 | 2.7 | 3.0 | 2.0 | 3.1 | 2.2 |
| Wet hair feel | 2.8 | 2.1 | 2.6 | 2.2 | 3.0 | 2.3 |
| Dry hair combability | 2.7 | 2.5 | 2.3 | 2.3 | 3.1 | 2.6 |
| Anti-electrost. effect | 1.1 | 1.1 | 1.8 | 1.8 | 1.7 | 1.3 |
| Hair handling | 2.4 | 2.2 | 2.6 | 2.3 | 2.3 | 2.1 |
| Dry hair feel | 2.4 | 2.4 | 2.1 | 1.9 | 2.6 | 2.4 |
| Wave-set duration | 2.3 | 2.0 | 2.4 | 2.3 | 2.2 | 2.1 |

The control values may obviously change, even though the formulation is the same, as the group of volunteers used for the study changes.

From Table 14 it can be seen how, even with a low concentration of use, the esters from alpha-hydroxyacids of the present invention (EMI, ETI and ESI products) on the whole have decisively positive tricological properties.

In the worst of hypotheses, the results obtained are equivalent to the commercial product (GAFQUAT$^R$ 755N), while in most cases much better values are observed for the parameters indicated in Table 14.

In particular the feel of both wet and dry hair (expression of the conditioning effect) proved to be extremely positive both in the case of EMI and in the case of ESI, products used in the formulations of the present invention.

What is claimed is:

1. A detergent composition, characterized in that said composition has no cationic surface-active agents, and consists of:

(a) surface-active agents selected from the group consisting of anionic, nonionic and amphoteric surface-active agents and relative mixtures;

(b) esters having the formula (I):

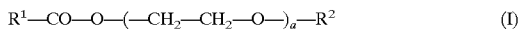

$$R^1\text{—CO—O—}(\text{—CH}_2\text{—CH}_2\text{—O—})_a\text{—}R^2 \qquad (I)$$

wherein:
a is between zero and 20;
$R^2$ is a mono-functional hydrocarbon radical, having from 6 to 20 carbon atoms;
$R^1$ is a mono-functional hydrocarbon radical having the formula:

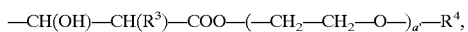

—CH(OH)—CH($R^3$)—COO—(—CH$_2$—CH$_2$—O—)$_{a'}$—$R^4$, wherein $R^3$=H or OH; a' is between 0 and 20, and $R^4$ is a monofunctional hydrocarbon radical having from 6 to 20 carbon atoms;
the weight ratio between the surface-active agents (a) and the esters having the formula (I) ranging from 1/1 to 600/1;
wherein the balance to 100% by weight of said composition consists of water and minor components selected from the group consisting of antifoaming agent, perfume, preservative and combinations thereof.

2. The composition according to claim 1, wherein the surface-active agents (a) are anionic.

3. The composition according to claim 1, wherein a=0.

4. The composition according to claim 3, wherein $R^2$ is a mono-functional alkyl radical having from 8 to 18 carbon atoms.

5. The composition according to claim 1, wherein $R^1$ is $-CH(OH)-CH(R^3)-COO-(-CH_2-CH_2-O-)_{a'}R^4$, wherein $R^3$=H or OH; a' is zero, and $R^4$ is a monofunctional alkyl radical having from 6 to 20 carbon atoms.

6. The composition according to claim 1, wherein the weight ratio between the surface-active agents (a) and the esters having the formula (I) ranges from 1.5/1 to 400/1.

7. A detergent formulation, consisting of the composition according to claim 1, wherein the ratio between the surface-active agents (a) and esters having the formula (I) ranges from 200/1 to 5/1 and wherein the concentration of the surface-active agents in the formulation ranges from 10 to 40%.

8. A softening agent formulation, consisting of the composition according to claim 1, wherein the ratio between surface-active agents (a) and esters having the formula (I) ranges from 50/1 to 0.75/1, and wherein the weight concentration of the surface-active agents (a) ranges from 2 to 8% by weight.

9. A textile finishing formulation, consisting of the composition according to claim 1, wherein the ratio between the surface-active agents (a) and esters having the formula (I) ranges from 10/1 to 1.5/1, and wherein the concentration of the surface-active agents (a) ranges from 3 to 10% by weight.

10. A hair shampoo formulation, consisting of the composition according to claim 1, wherein the ratio between surface-active agents (a) and esters having the formula (I) from 100/1 to 10/1, and wherein the concentration of surface-active agents (a) ranges from 7 to 20% by weight.

11. A detergent composition, wherein said composition contains no cationic surface-active agents, and comprises:
  (a) surface-active agents selected from the group consisting of anionic, nonionic and amphoteric surface-active agents and mixtures thereof;
  (b) esters having the formula (I):

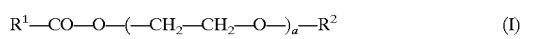

wherein:
  a is between zero and 20;
  $R^2$ is a mono-functional hydrocarbon radical, having from 6 to 20 carbon atoms;
  $R^1$ is a mono-functional hydrocarbon radical having the formula $-C_6H_n(OH)_m$, wherein n is between 3 and 4, m is between 1 and 2, the sum of m+n being equal to 5;
  wherein said ester having the formula (I) is not tridecyl salicylate;
  wherein the ratio between the surface-active agents (a) and esters having the formula (I) ranges from 100/1 to 10/1;
  and wherein the concentration of the surface-active agents (a) ranges from 10 to 40% by weight, the balance to 100 % by weight of said composition consisting of water and minor components.

12. A hair shampoo formulation, wherein said formulation contains no cationic surface-active agents, and comprises:
  (a) surface-active agents selected from the group consisting of anionic, nonionic and amphoteric surface-active agents and relative mixtures;
  (b) esters having the formula (I):

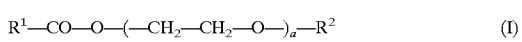

wherein:
  a is between zero and 20;
  $R^2$ is a mono-functional hydrocarbon radical, having from 6 to 20 carbon atoms;
  $R^1$ is a mono-functional hydrocarbon radical having the formula $-C_6H_n(OH)_m$, wherein n is between 3 and 4, m is between 1 and 2, the sum of m+n being equal to 5;
  wherein said ester having the formula (I) is not tridecyl salicylate;
  wherein the ratio between surface-active agents (a) and esters having the formula (I) ranges from 100/1 to 5/1; and
  wherein the concentration of surface-active agents ranges from 7 to 20% by weight.

13. The hair shampoo formulation according to claim 12, wherein the ratio between surface-active agents (a) and esters having the formula (I) ranges from 40/1 to 10/1.

14. The hair shampoo formulation according to claim 12, wherein the balance to 100% by weight of said formulation consists of water and minor components.

* * * * *